US012643844B2

(12) United States Patent
Sharratt

(10) Patent No.: US 12,643,844 B2
(45) Date of Patent: Jun. 2, 2026

(54) CATALYST AND PROCESS USING THE CATALYST

(71) Applicant: Mexichem Amanco Holding S.A. de C.V., Tlalnepantla (MX)

(72) Inventor: Andrew P. Sharratt, Cheshire (GB)

(73) Assignee: MEXICHEM AMANCO HOLDINGS S.A. DE C.V., Tlalnepantla (MX)

( * ) Notice: Subject to any disclaimer, the term of this patent is extended or adjusted under 35 U.S.C. 154(b) by 237 days.

(21) Appl. No.: 18/756,640

(22) Filed: Jun. 27, 2024

(65) Prior Publication Data

US 2024/0360056 A1 Oct. 31, 2024

Related U.S. Application Data

(60) Continuation of application No. 17/130,602, filed on Dec. 22, 2020, now Pat. No. 12,024,478, which is a
(Continued)

(30) Foreign Application Priority Data

Feb. 24, 2009 (GB) ...................................... 0903078

(51) Int. Cl.
*C07C 17/087* (2006.01)
*B01J 23/26* (2006.01)
(Continued)

(52) U.S. Cl.
CPC ............. *C07C 17/087* (2013.01); *B01J 23/26* (2013.01); *B01J 37/03* (2013.01); *B01J 37/26* (2013.01);
(Continued)

(58) Field of Classification Search
CPC ... B01J 23/26; B01J 37/03; B01J 37/26; B01J 35/615; B01J 35/613; C07C 17/087; C07C 17/10; C07C 17/206
(Continued)

(56) References Cited

U.S. PATENT DOCUMENTS 2,294,414 A 9/1942 Matuszk et al.
3,258,500 A 6/1966 Swamer et al.
(Continued)

FOREIGN PATENT DOCUMENTS

EP 0 714 874 A1 6/1996
EP 0 502 605 B1 7/1996
(Continued)

OTHER PUBLICATIONS

Erena et al., Study of the metallic function of Cr203—Zn0/ZSM5 bifunctional catalysts for the transformation of syngas . . . , AFINIFAD LIV, 471, Sep.-Oct. 1997, 367-371 +Eng Trans.
(Continued)

*Primary Examiner* — Patricia L. Hailey
(74) *Attorney, Agent, or Firm* — Crowell & Moring LLP; Yuezhong Feng

(57) ABSTRACT

A new chromium-containing fluorination catalyst is described. The catalyst comprises an amount of zinc that promotes activity and from 0.1 to 8.0% by weight of the chromium in the catalyst based on the total weight of the chromium is present as chromium (VI). The use of the zinc-promoted, chromium-containing catalyst in a fluorination process in which a hydrocarbon or halogenated hydrocarbon is reacted with hydrogen fluoride in the vapour-phase at elevated temperatures is also described.

20 Claims, 2 Drawing Sheets

Initial activity - Temperature required to achieve 10% 134a yield

Related U.S. Application Data continuation of application No. 15/816,307, filed on Nov. 17, 2017, now Pat. No. 10,906,853, which is a division of application No. 12/737,955, filed as application No. PCT/GB2009/002126 on Sep. 4, 2009, now Pat. No. 9,862,659.

(51) Int. Cl.

| | |
|---|---|
| *B01J 35/61* | (2024.01) |
| *B01J 37/03* | (2006.01) |
| *B01J 37/26* | (2006.01) |
| *C07C 17/10* | (2006.01) |
| *C07C 17/20* | (2006.01) |

(52) U.S. Cl.
CPC ............ *C07C 17/10* (2013.01); *C07C 17/206* (2013.01); *B01J 35/613* (2024.01); *B01J 35/615* (2024.01)

(58) Field of Classification Search
USPC .................................. 502/307, 319; 570/165
See application file for complete search history.

(56) References Cited

U.S. PATENT DOCUMENTS

| | | | |
|---|---|---|---|
| 4,792,643 | A | 12/1988 | Sobolev |
| 5,523,500 | A | 6/1996 | Cheminal et al. |
| 5,559,276 | A | 9/1996 | Scott et al. |
| 5,672,786 | A | 9/1997 | Bonniface et al. |
| 6,172,270 | B1 | 1/2001 | Tatematsu |
| 9,862,659 | B2 * | 1/2018 | Sharratt ................... B01J 37/03 |
| 10,906,853 | B2 * | 2/2021 | Sharratt ................... B01J 23/26 |
| 12,024,478 | B2 * | 7/2024 | Sharratt ................ C07C 17/206 |
| 2001/0011061 | A1 | 8/2001 | Scott et al. |
| 2004/0010168 | A1 | 1/2004 | Ramanathan et al. |
| 2005/0137082 | A1 | 6/2005 | Nojima et al. |
| 2007/0123742 | A1 | 5/2007 | Rao et al. |
| 2008/0299342 | A1 | 12/2008 | Schneider |
| 2009/0209792 | A1 | 8/2009 | Sharratt et al. |
| 2010/0210882 | A1 | 8/2010 | Sharratt et al. |
| 2011/0224466 | A1 | 9/2011 | Sharratt |
| 2012/0116131 | A1 | 5/2012 | Sharratt |

FOREIGN PATENT DOCUMENTS

| | | | |
|---|---|---|---|
| EP | 0 806 242 | A1 | 11/1997 |
| EP | 1 024 124 | A1 | 8/2000 |
| EP | 1 110 936 | A1 | 6/2001 |
| EP | 1 132 364 | A1 | 9/2001 |
| EP | 0 957 074 | B1 | 2/2003 |
| EP | 1 038 858 | B1 | 7/2014 |
| JP | H 02178237 | A | 7/1988 |
| JP | H 10-218804 | A | 8/1988 |
| JP | 01178237 | U | 5/1998 |
| JP | 2850907 | B2 | 1/1999 |
| WO | WO 1994/006558 | A1 | 3/1994 |
| WO | WO 1995/031283 | A1 | 11/1995 |
| WO | WO 1998/010862 | A1 | 3/1998 |
| WO | WO 2000/0002160 | | 4/2000 |
| WO | WO 2000/021660 | A1 | 4/2000 |
| WO | WO 2003/002251 | A2 | 1/2003 |
| WO | WO 2005/037431 | A1 | 4/2005 |
| WO | WO 2005/123791 | A1 | 12/2005 |
| WO | WO 2006/106353 | A1 | 10/2006 |
| WO | WO 2008/040969 | A2 | 4/2008 |
| WO | WO 2017/205273 | A1 | 11/2017 |

OTHER PUBLICATIONS

Arkema Opposition Statement, Mar. 15, 2022 (7 pages).
Machine Translation of Arkema Opposition Statement, Mar. 15, 2022 (7 pages).
Scott, W., "Thesis: Catalytic Fluorination of Haloethanes", Department of Chemistry, University of Glasqow, Feb. 1997 (227 pages).

* cited by examiner

Figure 1: Initial activity - Temperature required to achieve 10% 134a yield
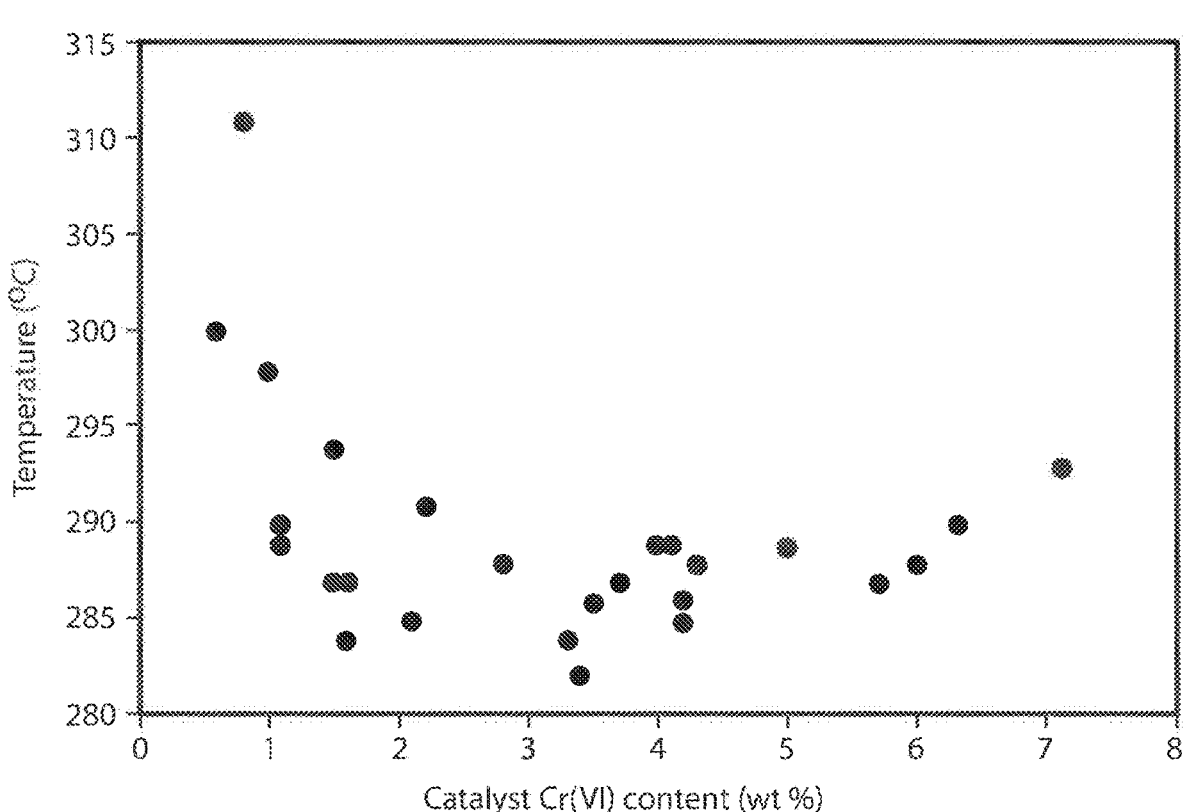

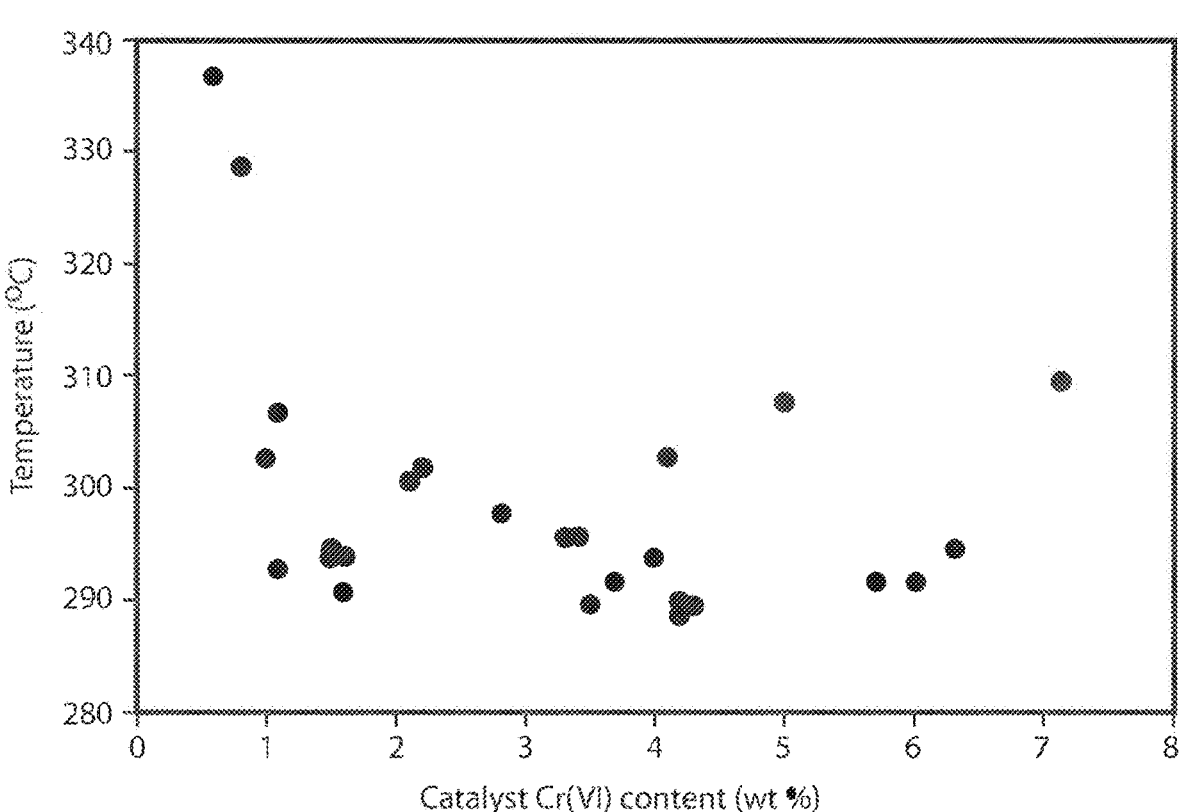
Figure 2: Stability - Temperature required to achieve 10% 134a yield

CATALYST AND PROCESS USING THE CATALYST

RELATED APPLICATIONS

This application is a continuation of U.S. application Ser. No. 17/130,602, filed Dec. 22, 2020, which is a continuation of U.S. application Ser. No. 15/816,307, filed Nov. 17, 2017, which is a divisional of U.S. patent application Ser. No. 12/737,955 filed May 16, 2011, which is the U.S. National Phase of International Application Serial No. PCT/GB2009/002126, filed Sep. 4, 2009, which claims priority to British application No. 0903078.4, filed Feb. 24, 2009, and British application No. 0816206.7, filed on May 9, 2008.

BACKGROUND OF THE INVENTION

This invention relates to a chromium-containing fluorination catalyst and to a process for the production of fluorinated hydrocarbons that uses the catalyst. More particularly, the invention relates to a zinc promoted, chromium-containing fluorination catalyst and to a process for the production of a fluorinated hydrocarbon in which an alkene or halogenated hydrocarbon is reacted with hydrogen fluoride in the presence of the catalyst.

The production of fluorinated hydrocarbons, which may also contain halogen atoms other than fluorine, by the catalysed vapour-phase fluorination of alkenes or halogenated hydrocarbons with hydrogen fluoride is well known and numerous catalysts have been proposed for use in such processes. Catalysts containing and typically based on chromium, and in particular chromia, are frequently employed in the known processes. Thus, for example, chromia or a halogenated chromia may be used in the vapour-phase reaction of trichloroethylene with hydrogen fluoride to produce 1-chloro-2,2,2-trifluoroethane as described in GB-1,307,224 and in the vapour-phase reaction of 1-chloro-2,2,2-trifluoroethane with hydrogen fluoride to produce 1,1,1,2-tetrafluoroethane as described in GB-1,589,924. The same catalyst may also be used for the fluorination of chlorodifluoroethylene to 1-chloro-2,2,2-trifluoroethane, for example in a process for the removal of chlorodifluoroethylene impurity from 1,1,2-tetrafluoroethane as also described in GB-1,589,924.

EP-A-0502605 discloses a chromium-containing fluorination catalyst which comprises an activity-promoting amount of zinc or a compound of zinc. The catalyst can be used in a process for preparing 1,1,1,2-tetrafluoroethane in which 1-chloro-2,2,2-trifluoroethane is reacted with hydrogen fluoride in the presence of the catalyst to produce the 1,1,1,2-tetrafluoroethane. The 1-chloro-2,2,2-trifluoroethane may be prepared by reacting trichloroethylene with hydrogen fluoride in the presence of the same catalyst.

Manufacturers of fluorinated hydrocarbons are always seeking improved catalysts for use in the manufacture of those compounds. It has now been found that the performance of chromium-containing catalysts containing controlled amounts of zinc may be augmented if some of the chromium in the catalyst is present as chromium (VI).

According to the present invention there is provided a chromium-containing fluorination catalyst which comprises an amount of zinc and wherein from 0.1 to 8.0% by weight of the chromium in the catalyst based on the total weight of said chromium is present as chromium (VI).

The present inventors have found that small amounts of chromium (VI) in the catalyst can improve catalyst activity and stability. This was unexpected as chromium (VI) is a strong oxidant and is known to promote the crystallisation of chromia into an unstable and inactive crystalline form. Thus, the present invention is concerned particularly with a chromium-containing fluorination catalyst which comprises an activity and stability promoting amount of chromium (VI) in an amount of from 0.1 to 8.0% by weight based on the total weight of chromium in the catalyst.

The present invention also provides a process for the production of fluorinated hydrocarbons which comprises reacting a hydrocarbon or a halogenated hydrocarbon with hydrogen fluoride in the vapour phase in the presence of a fluorination catalyst as herein defined.

In a preferred embodiment, the chromium-containing fluorination catalysts of the invention comprise one or more compounds selected from the chromium oxides, the chromium fluorides, fluorinated chromium oxides and the chromium oxyfluorides.

The chromium compounds which make up the chromium-containing catalyst of the invention can contain chromium in any of its usual oxidation states, namely chromium (II), chromium (III) and chromium (VI). However, the bulk of the chromium compounds in the catalyst will usually be based on chromium (III) and, of course, from 0.1 to 8.0% by weight of the chromium based on the total weight of chromium in the catalyst must be present as chromium (VI).

Chromium (III) typically comprises from 92.0 to 99.9% by weight, preferably from 94.0 to 99.9% by weight, e.g. from 95.0 to 99.5% by weight, particularly from 96.0 to 99.5% by weight and especially from 96.0 to 99.0% by weight, e.g. from 98.0 to 99.0% by weight of the total weight of chromium in the catalyst. Chromium (VI) comprises from 0.1 to 8.0% by weight, preferably from 0.1 to 6.0% by weight, e.g. from 0.5 to 5.0% by weight, particularly from 0.5 to 4.0% by weight and especially from 1.0 to 4.0% by weight, e.g. from 1.0 to 2.0% by weight of the total weight of chromium in the catalyst. As all the chromium is usually present as chromium compounds, the percentages quoted above will also normally define the amounts of chromium (III) and chromium (VI) compounds in the catalyst based on the total weight of chromium compounds.

Chromium (III) compounds that may be present in the chromium-containing catalyst of the invention include compounds selected from the group consisting of chromium (III) hydroxide, chromia (i.e. chromium (III) oxide), chromium (III) fluoride, fluorinated chromia and chromium (III) oxyfluorides. Chromium (VI) compounds that may be present in the catalyst include compounds selected from the group consisting of chromium (VI) oxide, chromic acid, fluorinated chromium (VI) oxide, chromium (VI) oxyfluorides and chromyl fluoride. The catalyst preferably contains one or more chromium (III) compounds and one or more chromium (VI) compounds selected from the above groups of compounds. The precise constitution of the catalyst will depend, inter alia, on the methods used for its preparation and whether the composition of the catalyst is measured pre- or post-fluorination.

DESCRIPTION OF THE DRAWING FIGURES

FIG. 1 is a graph depicting the temperature required to achieve a 10% R-134a yield using catalysts having various chromium (VI) content (wt %).

FIG. 2 is a further graph depicting the temperature required to achieve a 10% R-134a yield using catalysts having various chromium (VI) content (wt %)

DETAILED DESCRIPTION

Before the catalyst of the present invention is used in a fluorination process or before it is subjected to a fluorination pre-treatment, a significant proportion of the chromium, e.g. in excess of 50.0 weight % and more typically in excess of 75.0 weight % based on the total weight of chromium in the catalyst, is preferably present in the catalyst as chromium oxides, including chromia and chromium (VI) oxide. It may also contain an amount of chromium hydroxides, including chromium (III) and chromium (VI) hydroxides. The amounts of the chromium (III) oxides and hydroxides combined and the amounts of the chromium (VI) oxides and hydroxides combined are preferably as discussed above for the chromium (III) and chromium (VI) compounds generally. A preferred chromium-containing catalyst, pre-fluorination, has a molar ratio of chromium (III) to oxygen to hydroxyl species (Cr(III):O:OH) in the range of from 1:0.5:2 to 1:1.5:0, preferably in the range of from 1:1:1 to 1:1.5:0. This ratio can be readily determined using thermogravimetric analysis. In one particular embodiment, the chromium-containing catalyst, pre-fluorination, has a molar ratio of chromium (III) to oxygen to hydroxyl species (Cr(III):O:OH) in the range of from 1:0.5:2 to 1:n:m, preferably in the range of from 1:1:1 to 1:n:m, where n is less than 1.5, m is greater than zero and 2n+m=3.0.

When the catalyst is used in a fluorination process, or when it is subjected to a fluorination pre-treatment to be described hereinafter, a proportion of the chromium oxides in the catalyst and any chromium hydroxides that may be present will be converted to chromium fluorides, fluorinated chromium oxides and/or chromium oxyfluorides.

The zinc/chromia catalysts used in the present invention may be amorphous. By this we mean that the catalyst does not demonstrate substantial crystalline characteristics when analysed, for example, by X-ray diffraction.

Alternatively, the catalysts may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, and particularly from 0.4 to 5% by weight of one or more crystalline compounds of chromium and/or one or more crystalline compounds of zinc.

In a preferred embodiment, the catalyst of the invention is an amorphous or partially crystalline catalyst comprising less than 8.0% by weight, e.g. less than 5.0% by weight, of crystalline compounds of chromium and/or zinc based on the total weight of the catalyst. These catalysts preferably comprise greater than 3.0% by weight of zinc, e.g. from greater than 3.0 to 25.0% by weight, based on the total weight of the catalyst.

The amount of crystalline material in the catalysts of the invention can be determined by any suitable method known in the art. Suitable methods include X-ray diffraction (XRD). When XRD is used, the amount of crystalline material, such as the amount of crystalline chromium oxide, can be determined with reference to a known amount of graphite present in the catalyst (e.g. graphite used in producing catalyst pellets) or, more preferably, by comparison of the intensity of the XRD patterns of the sample materials with reference materials prepared by suitable internationally recognised bodies, for example NIST (National Institute of Standards and Technology), that contain a known amount of a crystalline material.

The zinc is usually present in the catalyst as a zinc compound and may be present in or on the chromium-containing catalyst, that is the zinc or compound of zinc may be incorporated in the chromium-containing catalyst or it may be supported on the surface of the catalyst, depending at least to some extent upon the particular method employed for preparing the catalyst. If the zinc is incorporated throughout the chromium-containing catalyst, as is preferred, then it is preferably substantially evenly distributed throughout the catalyst bulk.

In a preferred embodiment, the zinc is contained in aggregates which have a size across their largest dimension of up to 1 micron and which are evenly distributed throughout at least the surface region of the catalyst and wherein greater than 40 weight % of the aggregates contain a concentration of zinc that is within ±1 weight % of the modal concentration of zinc in those aggregates.

It has been found that the stability of chromium-containing catalysts incorporating controlled amounts of zinc can be improved if the distribution of zinc in the catalyst meets the above criteria.

By the surface region of the catalyst, we are intending to refer to that portion of the catalyst that will contact the hydrogen fluoride and organic reactants during use. The surface of a catalyst is generally that region where the coordination or valency of the atoms is not satisfied when compared to the bulk material.

In this embodiment, the zinc-containing aggregates are preferably evenly distributed throughout the entire catalyst bulk.

The aggregates have a size across their largest dimension of up to 1 micron (1 μm), preferably in the range of from 20 nm to 1 μm, and greater than 40 weight %, preferably greater than 50 weight %, more preferably greater than 60 weight % and especially greater 70 weight % of the aggregates contain a concentration of zinc that is within ±1 weight % of the modal concentration of zinc in those aggregates. In a preferred embodiment, greater than 80 weight %, more preferably greater than 85 weight %, and especially greater than 90 weight % of the aggregates contain a concentration of zinc that is within ±2 weight % of the modal concentration of zinc in those aggregates.

The modal concentration of zinc in the aggregates is that concentration of zinc that occurs most frequently in the aggregates expressed as a whole number.

By 'evenly distributed' we include 'substantially evenly distributed' and mean that the number or density of zinc-containing aggregates in each region of the catalyst surface or the catalyst bulk, where the zinc is dispersed throughout the entire catalyst, is substantially the same. For example, where the aggregates are only present at the catalyst surface, the number of aggregates in each square millimetre of the catalyst surface is within ±2% of the mean number of aggregates per square millimetre of the catalyst surface. Where the zinc-containing aggregates are distributed throughout the entire catalyst bulk, the number of aggregates in each square millimetre of the catalyst bulk is within ±2% of the mean number of aggregates per square millimetre of the catalyst bulk.

The zinc is typically present in the catalyst in an amount of from 0.5 to 25% by weight, e.g. from greater than 3 to 25% by weight, based on the total weight of the catalyst. The amount of zinc is important, because at the right levels it will promote the activity of the chromium-containing catalyst. Too much zinc, on the other hand, may result in a decrease rather than an increase in catalyst activity.

The amount of zinc which will promote catalyst activity and produce a catalyst having an activity that is greater than the chromium-containing catalyst alone depends, at least to some extent, on the surface area of the catalyst and whether the zinc is incorporated throughout the catalyst bulk or just supported on its surface. Generally, the larger the working surface area of the catalyst, the greater is the amount of zinc which will be required to promote catalyst activity. Furthermore, catalysts containing zinc incorporated throughout their bulk, i.e. at surface and non-surface locations, will tend to require larger amounts of zinc than those catalysts which only have zinc on their surface.

By way of example, in the case of a catalyst where the zinc is introduced by impregnation to reside predominantly at the catalyst surface, activity promoting amounts of zinc for a chromium-containing catalyst having a working surface area of between 20 and 50 m$^2$/g are usually in the range of from about 0.5% to about 6.0% by weight based on the total weight of the catalyst, preferably in the range of from about 1.0% to about 5.0% by weight and especially in the range of from about 2.0% to about 4.0% by weight.

However, for catalysts having larger working surface areas, for example greater than 100 m$^2$/g, and comprising zinc distributed throughout the catalyst bulk, the zinc may be present in an amount of from 5.0% to about 25.0% by weight based on the total weight of the catalyst, preferably in an amount of from 5.0 to 20.0% by weight and especially in an amount of from 5.0 to 10.0% by weight.

For catalysts having small working surface areas, i.e. less than 20 m$^2$/g, for example about 5 m$^2$/g, the amount of zinc may be as low as 0.5% to 1% by weight based on the total weight of the catalyst.

It should be understood that the amounts of zinc discussed above refer to the amount of zinc itself, whether present as elemental zinc or as a compound of zinc. Thus, where the zinc is present as a compound of zinc, as is usual, the amounts refer to the zinc provided by the zinc compound and not to the amount of the compound of zinc.

Preferred catalysts of the invention have a surface area in the range of from 20.0 to 300.0 m$^2$/g, more preferably in the range of from 100 to 250 m$^2$/g and particularly in the range of from 180 to 220 m$^2$/g. When referring to the surface area of the catalyst, we are referring to the surface area prior to any fluorination treatment when measured by BET nitrogen isotherm (see, for example, G C Bond, Heterogeneous Catalysis—Principles and Applications 1987). These catalysts preferably comprise from 0.5 to 25.0% by weight, e.g. from greater than 3.0% to 25.0% by weight, more preferably from 0.5 to 10.0% by weight, e.g. from greater than 3.0% to 10.0% by weight, and particularly from 1.0 to 6.0% by weight, e.g. from greater than 3.0% to 6.0% by weight of zinc based on the total weight of the catalyst. The zinc can be distributed throughout the catalyst at surface and non-surface locations or just at the surface.

Although the amount of zinc which will promote catalyst activity will vary depending, inter alia, on the surface area of the catalyst, upon the distribution of zinc in the catalyst and upon the method that is used to prepare the catalyst, for any particular catalyst and catalyst preparation method, the amount of zinc that will promote catalyst activity is readily determined by routine experimentation using the above percentages as a guide.

The chromium-containing catalyst may also comprise metal oxides, fluorinated metal oxides, metal fluorides or metal oxyfluorides other than chromium oxides, fluorinated chromium oxides, chromium fluorides or chromium oxyfluorides. The additional metal oxide may, for example, be selected from alumina, magnesia and zirconia, and in particular magnesia and alumina, which during operation of the catalyst may be converted at least in part to aluminium fluoride and magnesium fluoride respectively.

If desired, the catalyst may also contain one or more metals other than zinc, for example nickel, cobalt or other divalent metals. Preferably, however, the chromium-containing catalyst will comprise just zinc, either as a metal but more typically as one or more zinc compounds.

The chromium-containing catalyst of the invention may also be supported on a catalyst support material such as activated carbon or alumina.

The zinc promoter may be introduced into and/or onto the chromium-containing catalyst in the form of a compound, for example a halide, oxyhalide, oxide or hydroxide, depending at least to some extent upon the catalyst preparation technique employed. When the zinc promoter is introduced by impregnating a chromium-containing catalyst, e.g. one containing one or more chromium (III) compounds and one or more chromium (VI) compounds, with a zinc compound, the zinc compound is preferably a water-soluble salt, for example a halide, nitrate or carbonate, and is impregnated into the chromium-containing catalyst by contacting the catalyst with an aqueous solution or slurry of the zinc compound.

In an alternative method for preparing the catalyst of the invention, the hydroxides of zinc and chromium are co-precipitated and then converted to their oxides by calcination to prepare a mixed oxide catalyst.

If other metal oxides are to be included in the catalyst, such as alumina, then these can be introduced by co-precipitating the hydroxides of chromium and the other metal and then converting the hydroxides to their oxides by calcination to prepare a mixed oxide catalyst, e.g. of chromium and aluminium oxides such as chromia and alumina. Zinc can be introduced into the catalyst by impregnating the hydroxide or oxide mixture with an aqueous solution or dispersion of a zinc compound in the manner discussed above. Alternatively, zinc hydroxide can be co-precipitated with the hydroxides of chromium and the other metal and the three hydroxides then converted simultaneously to their oxides by calcination.

Mixing and milling of an insoluble zinc compound with the basic chromium containing catalyst provides a further method of preparing the catalyst.

In a preferred embodiment, the catalysts of the present invention are prepared by adding zinc and chromium (III) salts to water and then co-precipitating the hydroxides of zinc and chromium (III) by adding a suitable inorganic hydroxide and preferably ammonium hydroxide to the aqueous salt solution. The mixture of zinc and chromium hydroxides is then collected, e.g. by filtration, washed, dried and calcined to convert the hydroxides to their oxides. Any water soluble and stable salts of zinc and chromium can be used including the chlorides, carbonates and nitrates. Preferred salts of chromium include chromium nitrate and basic chromium nitrate (Cr(NO$_3$)$_2$·OH). A particularly suitable chromium salt is chromium (III) nitrate. A preferred zinc salt is zinc nitrate.

The co-precipitation is preferably conducted under mixing conditions that will result in a catalyst in which the zinc or at least the majority of the zinc is contained in aggregates which have a size across their largest dimension of up to 1 micron and which are evenly distributed throughout the entire catalyst bulk and wherein greater than 40 weight % of the zinc-containing aggregates contain a concentration of zinc that is within ±1 weight % of the modal concentration of zinc in the zinc-containing aggregates.

The washing process following collection of the mixed hydroxide precipitate can be important, because if the precipitate is prepared from a solution containing a nitrate salt then any nitrate that remains following the washing process can act as an oxidant to generate chromium (VI) from chromium (III) during the calcination process. More thorough washing of the collected precipitate, e.g. by repeated washing using fresh batches of washing liquor, will tend to reduce the residual nitrate levels and hence the amount of nitrate that is available to oxidise the chromium (III) during the calcination step. Furthermore, the nature of the washing medium can influence the efficacy with which nitrate contained in the mixed hydroxide precipitate is removed. For example, washing with an aqueous ammonia solution is more effective at removing the nitrate than water alone. Thus, if the mixed hydroxide precipitate is prepared from an aqueous solution containing chromium (III) and/or zinc nitrate, it is possible to control the level of chromium (VI) in the catalyst following calcination by exercising control over the washing process, which in turn will affect the residual level of nitrate in the precipitate that is available to oxidise the chromium (III).

Where a calcination step is employed in the production of the catalysts of the invention, as is preferred, it typically involves heating the precursor catalyst material at a temperature in the range of from 300 to 450° C., more preferably in the range of from 300 to 400° C., for example around 350° C. The calcination temperature that is used can also influence the level of chromium (VI) in the final catalyst. For example, if the catalyst is prepared by calcining a mixed hydroxide precipitate prepared from an aqueous solution containing chromium (III) and/or zinc nitrate, then for a given level of residual nitrate following washing, higher calcination temperatures will tend to result in more of the chromium (III) being oxidised to chromium (VI). The calcination may be conducted in an inert atmosphere, e.g. of nitrogen, or it may be conducted in air or in an atmosphere comprising air or oxygen in mixture with an inert gas such as nitrogen.

Another convenient way of generating the desired level of chromium (VI) compounds in the catalyst is by introducing a controlled amount of air into the calcination step to oxidise the requisite proportion of chromium (III) to chromium (VI). Here again, the calcination temperature that is used can also influence the level of chromium (VI) in the final catalyst, with higher calcination temperatures tending to encourage greater oxidation of the chromium (III) for a given level of air.

The fluorination catalyst will usually be subjected to a fluorination treatment by heating in the presence of hydrogen fluoride, and optionally an inert diluent, prior to being used in the catalysis of fluorination reactions. A typical fluorination treatment comprises heating the catalyst in the presence of hydrogen fluoride at a temperature in the range of from 250 to 450° C., more preferably in the range of from 300 to 380° C. and particularly in the range of from 350 to 380° C. In a preferred embodiment, the fluorination treatment is conducted by contacting the fluorination catalyst with a mixture of hydrogen fluoride and nitrogen. Conveniently, the treatment is conducted in the reactor in which the subsequent fluorination process is to be conducted by passing the hydrogen fluoride or hydrogen fluoride/nitrogen mixture through the reactor while it is heated.

Following the fluorination treatment, the working catalyst usually comprises at least a proportion of zinc fluoride in and/or on a fluorinated chromium-containing catalyst material comprising one or more fluorine-containing chromium (III) compounds and one or more fluorine-containing chromium (VI) compounds selected from the fluorinated chromium oxides, the chromium fluorides and the chromium oxyfluorides. Where the catalyst is a mixed oxide catalyst prepared by co-precipitation of chromium and zinc hydroxides followed by calcination to convert the hydroxides to their oxides, as is preferred, the fluorination treatment usually converts at least a proportion of the oxides to oxyfluorides and fluorides.

The catalyst may be in the form of pellets or granules of appropriate shape and size for use in a fixed bed or a fluidised bed. Conveniently the catalyst is in the form of cylindrically shaped pellets having a length and diameter in the range of from 1 to 6 mm, preferably in the range of from 2 to 4 mm, for example 3 mm.

After a period of use catalysing a fluorination reaction, the used catalyst may be regenerated or reactivated, for example by heating in air/nitrogen or air/hydrogen fluoride mixtures at a temperature of from about 300° C. to about 500° C. The regeneration or reactivation may be conducted periodically until the catalyst has reached the end of its useful lifetime. The catalyst may also be regenerated by passing chlorine through the reactor while heating the catalyst. Alternatively, the catalyst may be regenerated continuously while the process is being operated.

A further aspect of the present invention resides in the use of the zinc-promoted, chromium-containing catalyst in a fluorination process in which a hydrocarbon or halogenated hydrocarbon is reacted with hydrogen fluoride in the vapour-phase at elevated temperatures.

Accordingly, the present invention also provides a process for the production of fluorinated hydrocarbons which comprises reacting a hydrocarbon or a halogenated hydrocarbon with hydrogen fluoride at elevated temperature in the vapour phase in the presence of a fluorination catalyst as herein defined.

Alkenes and alkanes as well as their halogenated counterparts containing at least one chlorine atom may be fluorinated using hydrogen fluoride and the catalysts of the present invention. Examples of specific vapour phase fluorinations which may be effected are the production of 1,1,1,2-tetrafluoroethane from 1-chloro-2,2,2-trifluoroethane, the production of 1-chloro-2,2,2-trifluoroethane from trichloroethylene, the production of pentafluoroethane from dichlorotrifluoroethane, the production of dichlorotrifluoroethane, chlorotetrafluoroethane and/or pentafluoroethane from perchloroethylene and the conversion of 1-chloro-2,2-difluoroethylene to 1-chloro-2,2,2-trifluoroethane.

The fluorination conditions employed when reacting the hydrocarbon or halogenated hydrocarbon with hydrogen fluoride in the presence of the catalyst of the invention may be those known in the art for fluorination reactions that employ chromium-containing catalysts, for example atmospheric or super-atmospheric pressures and reactor temperatures in the range of from 180° C. to about 500° C. When referring to the reactor temperature, we are referring to the mean temperature within the catalyst bed. It will be appreciated that for an exothermic reaction, the inlet temperature will be lower than the mean temperature, and for an endothermic reaction, the inlet temperature will be greater than the mean. The precise conditions will depend, of course, upon the particular fluorination reaction being carried out.

In a preferred embodiment, the catalyst of the invention is used in a process for preparing 1,1,1,2-tetrafluoroethane which comprises reacting 1-chloro-2,2,2-trifluoroethane with hydrogen fluoride in the vapour phase at elevated temperatures in the presence of the catalyst. Reaction temperatures in the range of from 250 to 500° C. are typically employed, with reaction temperatures in the range of from 280 to 400° C. being preferred and reaction temperatures in the range of from 300 to 350° C. being especially preferred. The process may be carried out under atmospheric or super-atmospheric pressures. Pressures of from 0 to 30 barg are preferred whilst pressures of from 10 to 20 barg are especially preferred.

In a further preferred embodiment, the catalyst of the invention is used in a multi-step process for preparing 1,1,1,2-tetrafluoroethane which comprises reacting trichloroethylene with hydrogen fluoride in the presence of the catalyst to form 1-chloro-2,2,2-trifluoroethane. The 1-chloro-2,2,2-trifluoroethane is then reacted with further hydrogen fluoride in the presence of the catalyst to form the 1,1,1,2-tetrafluoroethane. The conversion of trichloroethylene to 1-chloro-2,2,2-trifluoroethane and the conversion of 1-chloro-2,2,2-trifluoroethane to 1,1,1,2-tetrafluoroethane may be conducted in discrete reaction zones of a single reactor, but they are preferably conducted in different reactors. Both reactions are conducted at elevated temperatures in the vapour phase.

The preferred pressure and temperature conditions for the conversion of 1-chloro-2,2,2-trifluoroethane to 1,1,1,2-tetrafluoroethane are as specified above.

For the conversion of trichloroethylene to 1-chloro-2,2,2-trifluoroethane, the process is typically conducted at a temperature in the range of from 180 to 300° C., preferably in the range of from 200 to 280° C. and particularly in the range of from 220 to 260° C. Atmospheric or super-atmospheric pressures may be employed in the process. Typically, the process is conducted at a pressure in the range of from 0 to 30 barg, preferably in the range of from 10 to 20 barg.

A particularly preferred embodiment of the above-described multi-step process for preparing 1,1,1,2-tetrafluoroethane from trichloroethylene comprises the steps of:

(A) in a first reaction zone reacting 1-chloro-2,2,2-trifluoroethane with hydrogen fluoride in the vapour phase in the presence of a fluorination catalyst of the invention at a temperature of from 250 to 450° C. so as to form a product mixture containing 1,1,1,2-tetrafluoroethane and hydrogen chloride together with unreacted starting materials;

(B) conveying the total product mixture of step (A) as well as trichloroethylene and optionally further hydrogen fluoride to a second reaction zone containing a fluorination catalyst of the invention and in said second reaction zone reacting the trichloroethylene with hydrogen fluoride in the vapour phase at 180 to 350° C. to form 1-chloro-2,2,2-trifluoroethane;

(C) collecting from step (B) a product mixture comprising 1-chloro-2,2,2-trifluoroethane, 1,1,1,2-tetrafluoroethane and hydrogen chloride;

(D) treating the product of step (C) to recover 1,1,1,2-tetrafluoroethane and produce a composition comprising 1-chloro-2,2,2-trifluoroethane that is suitable for conveying to the first reaction zone in step (A);

(E) conveying the 1-chloro-2,2,2-trifluoroethane composition obtained from step (D) optionally together with further hydrogen fluoride to said first reaction zone; and (F) collecting 1,1,1,2-tetrafluoroethane recovered in step (D).

Although the process described above refers to first and second reaction zones, this should not be taken as limiting the process to a particular order. In chemical terms, trichloroethylene is first converted to 1-chloro-2,2,2-trifluoroethane and the 1-chloro-2,2,2-trifluoroethane is then subsequently converted to 1,1,1,2-tetrafluoroethane. Thus, the first reaction in the reaction sequence is the hydrofluorination of trichloroethylene to form 1-chloro-2,2,2-trifluoroethane.

The first and second reaction zones may be provided by first and second reactors or they may be discrete zones of a single reactor. Preferably, the first and second reaction zones are provided by first and second reactors.

At least the stoichiometric amount of hydrogen fluoride is usually employed in step (A) of the above process. Typically, from 1 to 10 moles of hydrogen fluoride and preferably from 1 to 6 moles of hydrogen fluoride are used per mole of 1-chloro-2,2,2-trifluoroethane. Accordingly, the product mixture of step (A) will usually contain unreacted hydrogen fluoride in addition to 1,1,1,2-tetrafluoroethane, hydrogen chloride and by-products. It may also contain unreacted 1-chloro-2,2,2-trifluoroethane. Preferred reaction temperatures for step (A) are in the range of from 250 to 500° C., more preferably in the range of from 280 to 400° C. and particularly in the range of from 300 to 350° C. Preferred reaction pressures for step (A) are in the range of from 0 to 30 barg, more preferably in the range of from 10 to 20 barg, for example around 15 barg. Preferred residence times in the first reaction zone are in the range of from 1 to 600 seconds, more preferably in the range of from 1 to 300 seconds and particularly in the range of from 1 to 100 seconds.

In step (B), usually from 10 to 50 moles of hydrogen fluoride and preferably from 12 to 30 moles of hydrogen fluoride per mole of trichloroethylene are employed. Again, the reaction product of this stage will normally contain unreacted hydrogen fluoride and may also contain unreacted trichloroethylene. Preferred reaction temperatures for step (B) are in the range of from 180 to 300° C., more preferably in the range of from 200 to 300° C. and particularly in the range of from 220 to 280° C. Preferred reaction pressures for step (B) are in the range of from 0 to 30 barg, more preferably in the range of from 10 to 20 barg, for example around 15 barg. Preferred residence times in the first reaction zone are in the range of from 1 to 600 seconds, more preferably in the range of from 1 to 300 seconds and particularly in the range of from 1 to 100 seconds.

Although the reactant mixtures that are conveyed to the first and second reaction zones must include hydrogen fluoride, this does not mean that a fresh or virgin supply of material has to be delivered to both reaction zones. For example, the process can be operated so that virgin hydrogen fluoride is only introduced into the second reaction zone in sufficient excess that enough unreacted hydrogen fluoride can be recovered from the product mixture exiting step (B) to drive the hydrofluorination reaction that occurs in the first reaction zone in step (A). One possibility is to operate step (D) of the process so that the 1-chloro-2,2,2-trifluoroethane composition that is collected also contains hydrogen fluoride in a sufficient quantity for the reaction in the first reaction zone. Alternatively, the process can be operated so that virgin hydrogen fluoride is only introduced into the first reaction zone in sufficient excess that enough hydrogen fluoride remains in the product mixture of step (A) that is conveyed to the second reaction zone for reaction with the trichloroethylene. Additionally, after start up, the hydrogen fluoride required for the hydrofluorination reactions in the first and second reaction zones could even be introduced into a distillation column used to conduct step (D) of the process.

The reaction and separation steps which make up the preferred multi-step process for making 1,1,1,2-tetrafluoroethane may be performed using conventional equipment and techniques. Step (D), which is effectively a separation/purification step in which the useable components making up the product collected from step (B) are substantially separated from one another, may be effected by conventional distillation, phase separation and washing/scrubbing processes known to those skilled in the art.

The operation of the preferred multi-step process for making 1,1,1,2-tetrafluoroethane is described more particularly in EP-A-0449617.

In another preferred embodiment, the catalyst of the invention is used in a process for preparing pentafluoroethane which comprises reacting dichlorotrifluoroethane with hydrogen fluoride in the vapour phase at elevated temperatures in the presence of the catalyst. Reaction temperatures of at least 280° C., e.g. in the range of from 280 to 400° C., are typically employed, with reaction temperatures in the range of from 280 to 380° C. being preferred and reaction temperatures in the range of from 300 to 360° C. being especially preferred. The process may be carried out under atmospheric or super-atmospheric pressures. Typically, the process is conducted at a pressure of from 0 to 30 barg, preferably at a pressure of from 12 to 22 barg and more preferably at a pressure of from 14 to 20 barg.

In yet another preferred embodiment, the catalyst of the invention is used in a multi-step process for preparing pentafluoroethane which comprises reacting perchloroethylene with hydrogen fluoride in the presence of the catalyst to form dichlorotrifluoroethane. The dichlorotrifluoroethane is then reacted with further hydrogen fluoride in the presence of the catalyst to form the pentafluoroethane. The conversion of perchloroethylene to dichlorotrifluoroethane and the conversion of dichlorotrifluoroethane to pentafluoroethane may be conducted in discrete reaction zones of a single reactor, but they are preferably conducted in different reactors. Both reactions are conducted at elevated temperatures in the vapour phase.

The preferred pressure and temperature conditions for the conversion of dichlorotrifluoroethane to pentafluoroethane are as specified above.

For the conversion of perchloroethylene to dichlorotrifluoroethane, the process is typically conducted at a temperature in the range of from 200 to 350° C., preferably in the range of from 230 to 330° C. and particularly in the range of from 240 to 310° C. Atmospheric or super-atmospheric pressures may be employed in the process. Typically, the process is conducted at a pressure in the range of from 0 to 30 barg, preferably at a pressure in the range of from 10 to 20 barg and more preferably at a pressure in the range of from 12 to 18 barg.

A particularly preferred embodiment of the above-described multi-step process for preparing pentafluoroethane from perchloroethylene comprises the steps of:

(A) in a first reactor or a first plurality of reactors reacting perchloroethylene with hydrogen fluoride in the vapour phase at a temperature of from 200 to 350° C. in the presence of a chromium-containing fluorination catalyst of the invention to produce a composition comprising dichlorotrifluoroethane, hydrogen chloride, unreacted hydrogen fluoride and perchloroethylene, less than 2 weight % of chlorotetrafluoroethane and pentafluoroethane combined and less than 5 weight % of compounds having the formula $C_2Cl_{6-x}F_x$, where x is an integer of from 0 to 6, based on the total weight of organic compounds in the composition;

(B) subjecting the composition from step (A) to a separation step to yield a purified composition comprising at least 95 weight % of dichlorotrifluoroethane and less than 0.5 weight % of compounds having the formula $C_2Cl_{6-x}F_x$, where x is an integer of from 0 to 6, based on the total weight of organic compounds in the composition; and (C) in a second reactor or a second plurality of reactors reacting the composition from step (B) with hydrogen fluoride in the vapour phase at a temperature of at least 280° C. in the presence of a chromium-containing fluorination catalyst of the invention to produce a composition comprising pentafluoroethane and less than 0.5 weight % of chloropentafluoroethane, based on the total weight of organic compounds in the composition.

By compounds of formula $C_2Cl_{6-x}F_x$, where x is from 0 to 6, we include trichlorotrifluoroethane and dichlorotetrafluoroethane.

In step (A), from 3 to 50 moles of hydrogen fluoride are usually employed per mole of perchloroethylene. Preferably, from 4 to 20 moles of hydrogen fluoride and more preferably from 4 to 10 moles of hydrogen fluoride are used per mole of perchloroethylene. Preferred reaction temperatures and pressures for step (A) are as discussed above for the conversion of perchloroethylene to dichlorotrifluoroethane. Preferred residence times for the reactants in the first reactor in step (A) are in the range of from 10 to 200 seconds, more preferably in the range of from 30 to 150 seconds and particularly in the range of from 60 to 100 seconds.

In step (C), from 2 to 20 moles of hydrogen fluoride are usually employed per mole of dichlorotrifluoroethane. Preferably, from 2 to 10 moles of hydrogen fluoride and more preferably from 2 to 6 moles of hydrogen fluoride are used per mole of dichlorotrifluoroethane. Preferred reaction temperatures and pressures for step (C) are as discussed above for the conversion of dichlorotrifluoroethane to pentafluoroethane. Preferred residence times for the reactants in the second reactor in step (C) are in the range of from 10 to 200 seconds, more preferably in the range of from 20 to 100 seconds and particularly in the range of from 30 to 60 seconds.

The reaction and separation steps which make up the preferred multi-step process for making pentafluoroethane may be performed using conventional equipment and techniques. Separation step (B) may, for example, be effected using conventional distillation, phase separation and washing/scrubbing processes known to those skilled in the art.

The operation of the preferred multi-step process for making pentafluoroethane is described more particularly in WO 2007/068962.

It is preferred to operate processes that use the catalyst of the invention continuously, except for any shut-down time that is necessary to regenerate or reactivate a catalyst that has been deactivated though use. The feeding of air to the catalyst during operation of the process may counter catalyst deactivation and reduce the frequency of process shut-downs for catalyst regeneration.

The present invention is now illustrated but not limited by the following examples.

General Procedures

Catalyst Preparation:

A mixture of zinc and chromium (III) hydroxides was made by co-precipitation from an aqueous solution of zinc and chromium (III) nitrates using ammonium hydroxide (12.5% w/w ammonia in deionised water). The solution of zinc and chromium nitrates contained a chromium content of approximately 10% w/w and a zinc content of approximately 1.3% w/w to achieve a loading of zinc in the finished catalyst formulation of around 8.0 weight %. The equipment employed comprised a cooled and stirred 300 ml precipitation tank which was fed with an aqueous stream comprising the zinc and chromium nitrates and a separate stream of ammonium hydroxide. The tank stirrer was rotated at 500 rpm during catalyst preparation. The mixed-nitrates feed and ammonium hydroxide feed were injected continuously into the tank at a point close to the stirrer blade to ensure rapid mixing. The mixed-hydroxide product formed in the precipitation tank was collected at an overflow point which maintained a constant slurry volume of approximately 200 ml in the precipitation tank during a catalyst preparation. The vessel walls were cooled to maintain a temperature of 14 to 15° C. and the ammonium hydroxide pumping rate adjusted to maintain the pH of the slurry in the range of 7 to 8.5.

400 ml batches of slurry from the precipitation tank were filtered to recover the co-precipitated hydroxides, which were then washed and filtered further. The degree of washing was important, since it determined the residual level of oxidants and particularly nitrate salts that were available to generate the Cr(VI) during calcination. Either water or water doped with varying amounts of a 25% aqueous ammonia solution were used as the washing medium and either single or multiple washes were conducted.

The batches of washed solid were then dried at 100° C. overnight in a nitrogen atmosphere, powdered to pass through a 0.5 mm sieve and mixed with 2% w/w graphite. 2 to 3 g batches of this lubricated powder were then pressed into 13 mm diameter discs using an applied pressure of 5 tonnes. The compacted hydroxide discs were then crushed and sieved to generate particles in the size range 0.5 to 1.4 mm for calcination and subsequent catalyst testing.

6 g batches of the compacted and crushed hydroxide materials were charged to a 12.7 mm (½") diameter calcination tube purged with 60 ml/min of nitrogen. The catalyst batches were then calcined by heating to either 300° C. or 350° C. for a period of four hours and finally cooled under nitrogen to room temperature to generate the finished catalysts for performance testing. It is during the calcination stage that the Cr(VI) is generated.

Measurement of Chromium (VI) Content:

The chromium (VI) level in the catalyst samples was measured by reduction. A small sample of catalyst was loaded into an Inconel U-tube reactor and the reactor purged with a mixture of hydrogen (15 ml/min) and nitrogen (60 ml/min) at room temperature. The reduction was then initiated by placing the U-tube containing the catalyst into an oven pre-heated to 370° C. The gas stream exiting the reactor was fed to a gas chromatogram equipped with a thermal conductivity detector (TCD) to determine the amount of hydrogen consumed during the reduction from which the level of chromium (VI) in the catalyst could be calculated.

The chromium (VI) level could also be determined by reduction in a thermogravimetric analyser, using the weight loss to determine the chromium (VI) level.

Catalyst Testing:

The performance of the catalysts was investigated using a catalyst test rig that contained 4 reactor tubes each with independent HF and trichloroethylene feeds. Each reactor was charged with 2 g of catalyst in the particle size range 0.5 to 1.4 mm. Nitrogen at a flow rate of 60 ml/min was then directed to the reactor inlets and the catalyst samples dried in the nitrogen stream at 250° C. for 1 hour.

After drying, HF was fed to each reactor by means of a sparge system. A 5 ml/min flow of nitrogen was passed through liquid HF at a constant 8° C. to give a 30 ml/min flow of HF gas which was then passed to each reactor along with a 60 ml/min flow of nitrogen. The reactors were heated to 250° C. and the HF/nitrogen mixture passed over the catalyst samples for approximately 30 minutes until HF was observed in the reactor off gas. At this point, the 60 ml/min nitrogen flow was redirected to the reactor exit. The catalyst samples were then exposed to the HF:$N_2$ (30:5 ml/min) stream for a further one hour at 250° C. before ramping the temperature to 460° C. at 40° C. per hour then holding at 460° C. overnight.

The following day the reactors were cooled to 350° C. and trichloroethylene was fed to the catalyst in each reactor by sparging a 5 ml/min flow of nitrogen through liquid trichloroethylene (TRI) at room temperature to give a 1 ml/min flow of trichloroethylene gas. The catalyst was allowed to equilibrate in the HF:TRI:$N_2$ (30:1:10 ml/min) gas stream for about 2 hours before reducing the temperature to 300° C. The catalyst was allowed to equilibrate at 300° C. for about 1 hour before measuring the production of 1-chloro-2,2,2-trifluoroethane (R-133a) and 1,1,1,2-tetrafluoroethane (R-134a) by gas chromatography (GC). Using the R-134a yield, the temperature required to give a 10% 134a yield was then calculated.

The trichloroethylene feed was then switched off and the catalyst samples were thermochemically "aged" by heating them at 500° C. in the HF stream overnight. The reactors were then cooled to 350° C. and operated as before to prepare R-134a from trichloroethylene. The catalyst activity was investigated by determining the temperature required to give a 10% yield of R-134a from trichloroethylene. This activity was taken to be the initial activity of the catalyst, because catalysts tend to take some time to bed in before they operate at optimum levels.

The trichloroethylene feed was then switched off once again and the catalyst samples were thermochemically "aged" still further by heating them at 519° C. in the HF stream overnight. This additional ageing was conducted to investigate the stability of the catalysts. After the additional ageing, the reactors were cooled to 350° C. and operated as before to prepare R-134a from trichloroethylene. The stability of the catalysts was assessed by determining the temperature required to give a 10% yield of R-134a from trichloroethylene. After thermal ageing at 519° C., the more stable catalysts were those that gave a 10% conversion of trichloroethylene to R-134a at lower temperatures.

Example 1

A series of zinc promoted chromia catalysts were prepared using the above described general procedure. The washing of the filtered mixed hydroxide precipitates was varied from catalyst to catalyst, with both the washing medium and the number of washing cycles being varied. All the catalysts were calcined at 300° C. for 4 hours under nitrogen. The amount of chromium (VI) in the mixed oxide catalysts that were obtained following calcination was assessed using the general procedure described above.

The washing processes that were used and the amount of chromium (VI) in the resulting catalysts are reported in Table 1 below.

It is evident from the results reported in Table 1, that water doped with 25% aqueous ammonia is a more effective washing medium than water alone, removing more of the oxidising nitrate salts and giving rise to mixed oxide catalysts that under the same calcination conditions have smaller amounts of chromium (VI). It is also evident that multiple washing cycles will tend to remove more of the oxidising nitrate salts, once again resulting in catalysts that under the same calcination conditions have smaller amounts of chromium (VI).

It was found that the Cr(VI) levels in the final mixed oxide catalyst could be manipulated in the range 0 to 12 wt % by adjusting the washing procedure and washing medium.

Example 2

Two zinc promoted chromia catalysts were prepared using the above described general procedure. The washing of the filtered mixed hydroxide precipitates was the same in each case. One precipitate was calcined at 300° C. for 4 hours and the other at 350° C. for 4 hours. The amount of chromium (VI) in the mixed oxide catalysts that were obtained following calcination was then assessed using the general procedure described above. The results are reported in Table 2 below.

It is apparent from the results recorded in Table 2, that calcining at 350° C. instead of 300° C. caused a dramatic increase in the level of chromium (VI).

Example 3

A series of zinc promoted chromia catalysts were prepared using the above described general procedure. The washing of the filtered mixed hydroxide precipitates was varied from catalyst to catalyst in order to obtain mixed oxide catalysts with varying amounts of chromium (VI). All the catalysts were calcined at 300° C. The amount of chromium (VI) in the mixed oxide catalysts that were obtained following calcination was assessed using the general procedure described above.

Each catalyst was then tested in accordance with the general procedure described above to prepare R-134a from trichloroethylene.

The initial activity of the catalysts after ageing at 500° C. is recorded in FIG. 1. It is evident, that as the level of chromium (VI) in the catalyst is increased up to 8.0 weight %, that the temperature required to achieve a 10% R-134a yield reduces. Low operating temperatures indicate a more active catalyst, with reduced by-product formation and less fouling. Beyond around 4.0 weight %, the impact of further chromium (VI) is much less significant.

The stability of the catalysts after ageing at 519° C. is recorded) in FIG. 2. It is evident, that as the level of chromium (VI) in the catalyst is increased up to 8.0 weight % that lower temperatures were required to achieve a 10% R-134a yield. The effect beyond 4.0 weight % was much less significant. Thus, catalysts containing chromium (VI) exhibit greater stability. More stable catalysts means longer catalyst life and reduced costs.

TABLE 1

| pH during precipitation | Number of washes | Amount of 25% NH₃ added to wash water (g/l) | Cr(VI) wt % |
|---|---|---|---|
| 7-7.5 | 1 | 0 | 12.4 |
| 7-7.5 | 2 | 0 | 8.0 |
| 7-7.5 | 3 | 0 | 7.1 |
| 7-7.5 | 4 | 0 | 6.3 |
| 7-7.5 | 1 | 1 | 12.4 |
| 7-7.5 | 2 | 1 | 6.3 |
| 7-7.5 | 3 | 1 | 5.0 |
| 7-7.5 | 4 | 1 | 4.0 |
| 7-7.5 | 1 | 4 | 12.0 |
| 7-7.5 | 2 | 4 | 4.1 |

TABLE 1-continued

| pH during precipitation | Number of washes | Amount of 25% NH₃ added to wash water (g/l) | Cr(VI) wt % |
|---|---|---|---|
| 7-7.5 | 3 | 4 | 3.0 |
| 7-7.5 | 4 | 4 | 0.6 |
| 7-7.5 | 1 | 8 | 11.2 |
| 7-7.5 | 2 | 8 | 2.2 |
| 7-7.5 | 3 | 8 | 1.6 |
| 7-7.5 | 4 | 8 | 0.8 |

TABLE 2

| pH during precipitation | Number of washes | Amount of 25% NH₃ added to wash water (g/l) | Calcination Temperature (° C.) | Cr(VI) wt % |
|---|---|---|---|---|
| 7-7.5 | 4 | 4 | 300 | 0.6 |
| 7-7.5 | 4 | 4 | 350 | 3.3 |

I claim:

1. A method for preparing a chromium-containing fluorination catalyst, comprising:

adding an aqueous solution of one or more zinc compounds and chromium (III) compounds to a tank;

adding an aqueous solution of hydroxide to the tank while agitating the tank to provide a slurry of a precipitate mixture of zinc hydroxide and chromium (III) hydroxide;

isolating the precipitate mixture from the slurry;

washing the precipitate mixture; and calcining the precipitate mixture to provide the fluorination catalyst;

wherein the fluorination catalyst comprises chromium (III) in an amount of from 92.0 to 99.5% by weight of a total weight of chromium in the fluorination catalyst and chromium (VI) in an amount of from 0.1 to 8.0% by weight of the total weight of chromium in the fluorination catalyst.

2. The method of claim 1, wherein the aqueous solution of the one or more zinc compounds and chromium (III) compounds comprises about 10% by weight of chromium (III) and/or about 1.3% by weight of zinc.

3. The method of claim 1, wherein the aqueous solution of hydroxide comprises ammonium hydroxide.

4. The method of claim 3, wherein the adding the aqueous solution of hydroxide is at a rate so as to maintain a pH of the slurry in a range of from about 7 to about 8.5.

5. The method of claim 1, wherein the agitating comprises rotating at about 500 rpm.

6. The method of claim 1, wherein the adding of the aqueous solution of one or more zinc compounds and chromium (III) compounds and the adding of the aqueous solution of hydroxide was continuous.

7. The method of claim 6, further comprising maintaining a constant volume of the slurry in the tank.

8. The method of claim 6, further comprising collecting from the tank an overflow volume of the slurry before the isolating, the overflow volume in excess of the constant slurry volume.

9. The method of claim 1, wherein the isolating comprises filtering the slurry to provide the precipitate mixture.

10. The method of claim 1, wherein the washing comprises washing the precipitate mixture with water doped with a 25% aqueous ammonia solution.

11. The method of claim 10, wherein the water is doped with from about 4 grams to about 8 grams of 25% ammonia per liter of solution.

12. The method of claim 1, further comprising drying the precipitate mixture in a nitrogen atmosphere to provide a dried precipitate prior to calcining.

13. The method of claim 12, further comprising preparing pellets of length and diameter of from about 1 millimeter to about 6 millimeters.

14. The method of claim 13, wherein the preparing comprises:

pulverizing the dried precipitate to provide a powder;

mixing the powder with graphite to provide a powder mixture;

pressing the powder mixture into a disc; and crushing the disc to generate the particles.

15. The method of claim 14, wherein the powder mixture comprises about 2% by weight of graphite.

16. The method of claim 1, wherein the calcining comprises heating to at least about 300° C.

17. The method of claim 16, wherein the calcining comprises heating to at least about 350° C.

18. The method of claim 1, wherein the calcining is under nitrogen for at least about 4 hours.

19. The method of claim 1, wherein the washing comprises washing the precipitate mixture at least twice.

20. The method of claim 1, further comprising cooling under nitrogen after the calcining.

\* \* \* \* \*